(12) United States Patent
Hitoshi et al.

(10) Patent No.: US 7,090,990 B2
(45) Date of Patent: Aug. 15, 2006

(54) NP95: METHODS OF ASSAYING FOR CELL CYCLE MODULATORS

(75) Inventors: Yasumichi Hitoshi, Mountain View, CA (US); Yonchu Jenkins, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 427 days.

(21) Appl. No.: 10/123,568

(22) Filed: Apr. 15, 2002

(65) Prior Publication Data

US 2003/0194713 A1 Oct. 16, 2003

(51) Int. Cl.
*G01N 33/574* (2006.01)
(52) U.S. Cl. .............. 435/7.23; 435/7.1; 435/7.2; 530/350; 514/12; 536/23.1; 536/23.5
(58) Field of Classification Search ............... 435/7.1, 435/7.2, 7.23; 530/350; 514/12; 536/23.1, 536/23.5
See application file for complete search history.

(56) References Cited

OTHER PUBLICATIONS

Stein and Young, Science vol. 261 p. 1004 (1993).*
Skolnick et al TIBTECH vol. 18 p. 34 (2000).*
Citterio et al Molecular and Cellular Biology vol. 24 p. 2526 (2004).*
Fujimori, A. et al "Cloning anf Mapping of *Np95* Gene Which Encodes a Novel Nuclear Protein Associated with Cell Proliferation," *Mammalian Genome* 1998, pp. 1032-1035, vol. 9.
Miura, M. et al. "Dynamic Changes in Subnuclear NP95 Location During the Cell Cycle and Its Spatial Relationship with DNA Replication Foci," *Exper. Cell Res.* 2001, pp. 202-208, vol. 263.
Uemura, T. et al. "Temporal and Spatial Localization of Novel Nuclear Protein NP95 in Mitotic and Meiotic Cells," *Cell Structure & Function* 2000, pp. 149-159, vol. 25.

* cited by examiner

*Primary Examiner*—Sheela J. Huff
(74) *Attorney, Agent, or Firm*—Townsend and Townsend and Crew LLP

(57) ABSTRACT

The present invention relates to regulation of cellular proliferation. More particularly, the present invention is directed to nucleic acids encoding NP95, which is involved in modulation of cell cycle arrest. The invention further relates to methods for identifying and using agents, including small molecule chemical compositions, antibodies, peptides, cyclic peptides, nucleic acids, RNAi, antisense nucleic acids, and ribozymes, that modulate cell cycle arrest via modulation of NP95; as well as to the use of expression profiles and compositions in diagnosis and therapy related to cell cycle regulation and modulation of cellular proliferation, e.g., for treatment of cancer and other diseases of cellular proliferation.

25 Claims, 4 Drawing Sheets

SEQ ID NO:1
Size: 437
DNA--NP95

```
   1 CGACTCCTTA GAGCATGGCA TGGCTCAGAG GTGCTGGTAA AACTGATGGG GGTTTTTGCT
  61 GTCCCTCCCC TCAGCGCCGA CACCATGTGG ATCCAGGTTC GGACCATGGA CGGGAGGCAG
 121 ACCCACACGG TGGACTCGCT GTCCAGGCTG ACCAAGGTGG AGGAGCTGAG GCGGAAGATC
 181 CAGGAGCTGT TCCACGTGGA GCCAGGCCTG CAGAGGCTGT TCTACAGGGG CAAACAGATG
 241 GAGGACGGCC ATACCCTCTT CGACTACGAG GTCCGCCTGA TGACACCAT CCAGCTCCTG
 301 GTCCGCCAGA GCCTCGTGCT CCCCCACAGC ACCAAGGAGC GGGACTCCGA GCTCTCCGAC
 361 ACCGACTCCG GCTGCTGCCT GGGCCAGAGT GAGTCAGACA AGTCCTCCAC CCACGGCGAG
 421 GCGGCCGCCG AGACTGACAG CAGGCCAGCC GATGAGGACA TGTGGGATGA GACGGAATTG
 481 GGGCTGTACA AGGTCAATGA GTACGTCGAT GCTCGGGACA CGAACATGGG GGCGTGGTTT
 541 GAGGCGCAGG TGGTCAGGGT GACGCGGAAG GCCCCCTCCC GGGACGAGCC CTGCAGCTCC
 601 ACGTCCAGGC CGGCGCTGGA GGAGGACGTC ATTTACCACG TGAAATACGA CGACTACCCG
 661 GAGAACGGCG TGGTCCAGAT GAACTCCAGG GACGTCCGAG CGCGCGCCCG CACCATCATC
 721 AAGTGGCAGG ACCTGGAGGT GGGCCAGGTG GTCATGCTCA ACTACAACCC CGACAACCCC
 781 AAGGAGCGGG GCTTCTGGTA CGACGCGGAG ATCTCCAGGA AGCGCGAGAC CAGGACGGCG
 841 CGGGAACTCT ACGCCAACGT GGTGCTGGGG GATGATTCTC TGAACGACTG TCGGATCATC
 901 TTCGTGGACG AAGTCTTCAA GATTGAGCGG CCGGGTGAAG GGAGCCCCAT GGTTGACAAC
 961 CCCATGAGAC GGAAGAGCGG GCCGTCCTGC AAGCACTGCA AGGACGACGT GAACAGACTC
1021 TGCCGGGTCT GCGCCTGCCA CCTGTGCGGG GGCCGGCAGG ACCCCGACAA GCAGCTCATG
1081 TGCGATGAGT GCGACATGGC CTTCCACATC TACTGCCTGG ACCCGCCCCT CAGCAGTGTT
1141 CCCAGCGAGG ACGAGTGGTA CTGCCCTGAG TGCCGGAATG ATGCCAGCGA GGTGGTACTG
1201 GCGGGAGAGC GGCTGAGAGA GAGCAAGAAG AAGGCGAAGA TGGCCTCGGC CACATCGTCC
1261 TCACAGCGGG ACTGGGGCAA GGGCATGGCC TGTGTGGGCC GCACCAAGGA ATGTACCATC
1321 GTCCCGTCCA ACCACTACGG ACCCATCCCG GGGATCCCCG TGGGCACCAT GTGGCGGTTC
1381 CGAGTCCAGG TCAGCGAGTC GGGTGTCCAT CGGCCCCACG TGGCTGGCAT ACACGGCCGG
1441 AGCAACGACG GAGCGTACTC CCTAGTCCTG GCGGGGGGCT ATGAGGATGA CGTGGACCAT
1501 GGGAATTTTT TCACATACAC GGGTAGTGGT GGTCGAGATC TTTCCGGCAA CAAGAGGACC
1561 GCGGAACAGT CTTGTGATCA GAAACTCACC AACACCAACA GGGCGCTGGC TCTCAACTGC
1621 TTTGCTCCCA TCAATGACCA AGAAGGGGCC GAGGCCAAGG ACTGGCGGTC GGGGAAGCCG
1681 GTCAGGGTGG TGCGCAATGT CAAGGGTGGC AAGAATAGCA AGTACGCCCC CGCTGAGGGC
1741 AACCGCTACG ATGGCATCTA CAAGGTTGTG AAATACTGGC CCGAGAAGGG GAAGTCCGGG
1801 TTTCTCGTGT GGCGCTACCT TCTGCGGAGG ACGATGATG AGCCTGGCCC TTGGACGAAG
1861 GAGGGGAAGG ACCGGATCAA GAAGCTGGGG CTGACCATGC AGTATCCAGA AGGCTACCTG
1921 GAAGCCCTGG CCAACCGAGA GCGAGAGAAG GAGAACAGCA AGAGGGAGGA GGAGGAGCAG
1981 CAGGAGGGGG GCTTCGCGTC CCCCAGGACG GGCAAGGGCA AGTGGAAGCG GAAGTCGGCA
2041 GGAGGTGGCC CGAGCAGGGC CGGGTCCCCG CGCCGGACAT CCAAGAAAAC CAAGGTGGAG
2101 CCCTACAGTC TCACGGCCCA GCAGAGCAGC CTCATCAGAG AGGACAAGAG CAACGCCAAG
2161 CTGTGGAATG AGGTCCTGGC GTCACTCAAG GACCGGCCGG CGAGCGGCAG CCCCGTTCCAG
2221 TTGTTCCTGA GTAAAGTGGA GGAGACGTTC CAGTGTATCT GCTGTCAGGA GCTGGTGTTC
2281 CGGCCCATCA CGACCGTGTG CCAGCACAAC GTGTGCAAGG ACTGCCTGGA CAGATCCTTT
2341 CGGGCACAGG TGTTCAGCTG CCCTGCCTGC CGCTACGACC TGGGCCGCAG CTATGCCATG
2401 CAGGTGAACC AGCCTCTGCA GACCGTCCTC AACCAGCTCT TCCCCGGCTA CGGCAATGGC
2461 CGGTGATCTC CAAGCACTTC TCGACAGGCG TTTTGCTGAA AACGTGTCGG AGGGCTCGTT
2521 CATCGGCACT GATTTGTTC TTAGTGGGCT TAACTTAAAC AGGTAGTGTT CCTCCGTTC
2581 CCTAAAAAGG TTTGTCTTCC TTTTTTTTA TTTTTATTTT TCAAATCTAT ACATTTTCAG
2641 GAATTTATGT ATTCTGGCTA AAAGTTGGAC TTCTCAGTAT TGTGTTTAGT TCTTTGAAAA
2701 CATAAAAGCC TGCAATTTCT CGACAAAACA ACACAAGATT TTTTAAAGAT GGAATCAGAA
2761 ACTACGTGGT GTGGAGGCTG TTGATGTTTC TGGTGTCAAG TTCTCAGAAG TTGCTGCCAC
2821 CAACTCTTTA AGAAGGCGAC AGGATCAGTC CTTCTCTAGG GTTCTGGCCC CCAAGGTCAG
2881 AGCAAGCATC TTCCTGACAG CATTTTGTCA TCTAAAGTCC AGTGACATGG TTCCCCGTGG
2941 TGGCCCGTGG CAGCCCGTGG CATGGCGTGG CTCAGCTGTC TGTTGAAGTT GTTGCAAGGA
3001 AAAGAGGAAA CATCTCGGGC CTAGTTCAAA CCTTTGCCTC AAAGCCATCC CCACCAGAC
3061 TGCTTAGCGT CTGAGATCCG CGTGAAAGT CCTCTGCCCA CGAGAGCAGG GAGTTGGGGC
3121 CACGCAGAAA TGGCCTCAAG GGGACTCTGC TCCACGTGGG GCCAGGCGTG TGACTGACGC
```

FIG. 1
(Page 1 of 2)

```
3181  TGTCCGACGA  AGGCGGCCAC  GGACGGACGC  CAGCACACGA  AGTCACGTGC  AAGTGCCTTT
3241  GATTCGTTCC  TTCTTTCTAA  AGACGACAGT  CTTTGTTGTT  AGCACTGAAT  TATTGAAAAT
3301  GTCAACCAGA  TTCTAGAAAC  TGCGGTCATC  CAGTTCTTCC  TGACACCGGA  TGGGTGCTTG
3361  GGAACCGTTT  GAGCCTTATA  GATCATTTAC  ATTCAATTTT  TTTAACTCAG  CAAGTGAGAA
3421  CTTACAAGAG  GGTTTTTTTT  TAATTTTTTT  TTCTCTTAAT  GAACACATTT  TCTAAATGAA
3481  TTTTTTTTGT  AGTTACTGTA  TATGTACCAA  GAAAGATATA  ACGTTAGGGT  TTGGTTGTTT
3541  TTGTTTTTGT  ATTTTTTTTC  TTTTGAAAGG  GTTTGTTAAT  TTTTCTAATT  TTACCAAAGT
3601  TTGCAGCCTA  TACCTCAATA  AAACAGGGAT  ATTTTAAATC  ACATACCTGC  AGACAAACTG
3661  GAGCAATGTT  ATTTTTAAAG  GGTTTTTTTC  ACCTCCTTAT  TCTTAGATTA  TTAATGTATT
3721  AGGGAAGAAT  GAGACAATTT  TGTGTAGGCT  TTTTCTAAAG  TCCAGTACTT  TGTCCAGATT
3781  TTAGATTCTC  AGAATAAATG  TTTTTCACAG  ATTGAAAAAA  AAAAAAA
```

SEQ ID NO:2
Size: 135
PRT--NP95

MWIQVRTMDGRQTHTVDSLSRLTKVEELRRKIQELFHVEPGLQRLFYRGKQMEDGHTLFDYEVRLNDTIQLLVRQ
SLVLPHSTKERDSELSDTDSGCCLGQSESDKSSTHGEAAAETDSRPADEDMWDETELGLYKVNEYVDARDTNMGA
WFEAQVVRVTRKAPSRDEPCSSTSRPALEEDVIYHVKYDDYPENGVVQMNSRDVRARARTIIKWQDLEVGQVVML
NYNPDNPKERGFWYDAEISRKRETRTARELYANVVLGDDSLNDCRIIFVDEVFKIERPGEGSPMVDNPMRRKSGP
SCKHCKDDVNRLCRVCACHLCGGRQDPDKQLMCDECDMAFHIYCLDPPLSSVPSEDEWYCPECRNDASEVVLAGE
RLRESKKKAKMASATSSSQRDWGKGMACVGRTKECTIVPSNHYGPIPGIPVGTMWRFRVQVSESGVHRPHVAGIH
GRSNDGAYSLVLAGGYEDDVDHGNFFTYTGSGGRDLSGNKRTAEQSCDQKLTNTNRALALNCFAPINDQEGAEAK
DWRSGKPVRVVRNVKGGKNSKYAPAEGNRYDGIYKVVKYWPEKGKSGFLVWRYLLRRDDDEPGPWTKEGKDRIKK
LGLTMQYPEGYLEALANREREKENSKREEEEQQEGGFASPRTGKGKWKRKSAGGGPSRAGSPRRTSKKTKVEPYS
LTAQQSSLIREDKSNAKLWNEVLASLKDRPASGSPFQLFLSKVEETFQCICCQELVFRPITTVCQHNVCKDCLDR
SFRAQVFSCPACRYDLGRSYAMQVNQPLQTVLNQLFPGYGNGR

G1-2635 / Np95

The G1-2635 sequence is identical to a nuclear zinc finger protein, Np95, 793aa

Orientation of cDNA: Sense

Pfam HMM search was done at the Washington University web site

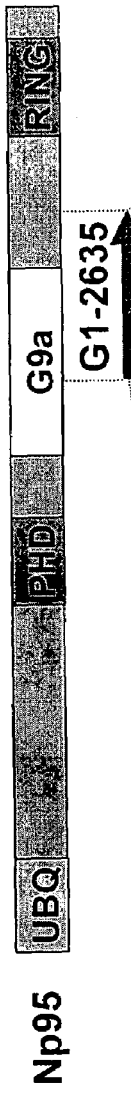

506:AEQSCDQKLTNTNRALALNCFAPINDQEGAEAKDWRSGKPVRVVR
NVKGGKINSKYAPAEGNRYDGIYKVVKYWPEKGKSGFLVWRYLLRRDD
DEPGPWTKEGKDRIKKLGLTMQYPEGYLEALANREREKENSKRE

UBQ(14-89): Ubiquitin like domain,
PHD(330-379): PHD-Zn finger, It could be important for the assembly or activity of multicomponent complexes
G9a(427-599): It is found in a nuclear protein associated with cell proliferation
RING(737-775): Zinc finger, C3HC4 type (RING finger), E3 ubiquitin-protein ligase activity is intrinsic to the RING domain of c-Cbl and is likely to be a general function of this domain; Various RING fingers exhibit binding to E2 ubiquitin-conjugating enzymes

FIG. 2

NP95: METHODS OF ASSAYING FOR CELL CYCLE MODULATORS

CROSS-REFERENCES TO RELATED APPLICATIONS

Not applicable.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to regulation of cellular proliferation. More particularly, the present invention is directed to nucleic acids encoding NP95, which is involved in modulation of cell cycle arrest. The invention further relates to methods for identifying and using agents, including small molecule chemical compositions, antibodies, peptides, cyclic peptides, nucleic acids, RNAi, antisense nucleic acids, and ribozymes, that modulate cell cycle arrest via modulation of NP95; as well as to the use of expression profiles and compositions in diagnosis and therapy related to cell cycle regulation and modulation of cellular proliferation, e.g., for treatment of cancer and other diseases of cellular proliferation.

BACKGROUND OF THE INVENTION

Cell cycle regulation plays a critical role in neoplastic disease, as well as disease caused by non-cancerous, pathologically proliferating cells. Normal cell proliferation is tightly regulated by the activation and deactivation of a series of proteins that constitute the cell cycle machinery. The expression and activity of components of the cell cycle can be altered during the development of a variety of human disease such as cancer, cardiovascular disease, psoriasis, where aberrant proliferation contributes to the pathology of the illness. There are genetic screens to isolate important components for cell cycle regulation using different organisms such as yeast, worms, flies, etc. However, involvement of a protein in cell cycle regulation in a model system is not always indicative of its role in cancer and other proliferative disease. Thus, there is a need to establish screening for understanding human diseases caused by disruption of cell cycle regulation. Identifying proteins, their ligands and substrates, and downstream signal transduction pathways involved in cell cycle regulation and neoplasia in humans is important for developing therapeutic regents to treat cancer and other proliferative diseases.

BRIEF SUMMARY OF THE INVENTION

The present invention therefore provides nucleic acids encoding NP95, which is a nuclear zinc finger protein involved in modulation of cell cycle arrest in tumor cells. The invention therefore provides methods of screening for compounds, e.g., small organic molecules, antibodies, peptides, cyclic peptides, nucleic acids, antisense molecules, RNAi, and ribozyme, that are capable of modulating cellular proliferation and/or cell cycle regulation, e.g., either inhibiting cellular proliferation, or activating apoptosis. Therapeutic and diagnostic methods and reagents are also provided. Modulators of NP95 are therefore useful in treatment of cancer and other proliferative diseases.

One embodiment of the present invention provides a method for identifying a compound that modulates cell cycle arrest. A cell comprising an NP95 polypeptide or fragment thereof is contacted with the compound. The NP95 polypeptide or fragment thereof may be encoded by a nucleic acid that hybridizes under stringent conditions to a nucleic acid encoding a polypeptide having an amino acid sequence of SEQ ID NO:2. The chemical or phenotypic effect of the compound upon the cell comprising the NP95 polypeptide or fragment thereof is determined, thereby identifying a compound that modulates cell cycle arrest. The chemical or phenotypic effect may be determined by measuring ubiquitin ligase activity of the NP95 polypeptide. The chemical or phenotypic effect may be determined by measuring cell cycle arrest. The cell cycle arrest may be measured by assaying DNA synthesis or fluorescent marker level. DNA synthesis may be measured by 3H thymidine incorporation, BrdU incorporation, or Hoescht staining. The fluorescent marker may be a cell tracker dye or green fluorescent protein. Modulation may be activation of cell cycle arrest or activation of cancer cell cycle arrest. The host cell may be a cancer cell. The cancer cell may be a breast, prostate, colon, or lung cancer cell. The cancer cell may be a transformed cell line, such as, for example, PC3, H1299, MDA-MB-231, MCF7, A549, or HeLa. The cancer cell may be p53 null, p53 mutant, or p53 wild-type. The polypeptide may be recombinant. The polypeptide may be encoded by a nucleic acid comprising a sequence of SEQ ID NO:1. The compound may be an antibody, an antisense molecule, a small organic molecule, a peptide, or a circular peptide.

Another embodiment of the invention provides a method for identifying a compound that modulates cell cycle arrest. The compound is contacted with an NP95 polypeptide or a fragment thereof, the NP95 polypeptide or fragment thereof. The NP95 polypeptide or a fragment thereof may be encoded by a nucleic acid that hybridizes under stringent conditions to a nucleic acid encoded by a polypeptide comprising an amino acid sequence of SEQ ID NO:2. The physical effect of the compound upon the NP95 polypeptide is determined. The chemical or phenotypic effect of the compound upon a cell comprising an NP95 polypeptide or fragment thereof is determined, thereby identifying a compound that modulates cell cycle arrest.

Yet another embodiment of the invention provides a method of modulating cell cycle arrest in a subject. A therapeutically effective amount of a compound identified according to one of the methods described above is administered to the subject. The subject may be a human. The subject may have cancer. The compound may inhibit cancer cell proliferation.

Even another embodiment of the invention provides a method of modulating cell cycle arrests in a subject. A therapeutically effective amount of a NP95 polypeptide is administered to the subject. The NP95 polypeptide may be encoded by a nucleic acid that hybridizes under stringent conditions to a nucleic acid encoding a polypeptide having an amino acid sequence of SEQ ID NO:2.

A further embodiment of the invention provides a method of modulating cell cycle arrest in a subject. A therapeutically effective amount of a NP95 polypeptide is administered to the subject. The NP95 polypeptide may be encoded by a nucleic acid that hybridizes under stringent conditions to a nucleic acid encoding a polypeptide having an amino acid sequence of SEQ ID NO:2.

Other embodiments and advantages of the present invention will be apparent from the detailed description that follows.

BRIEF DESCRIPTION OF THE DRAWINGS

FIG. 1 provides a nucleotide (SEQ ID NO:1) and amino acid sequence (SEQ ID NO:2) of human NP95.

FIG. 2 provides an illustration of the relevant domains of NP95, including the ubiquitin like domain, the zinc finger domain, the nuclear protein domain, and the ubiquitin ligase domain. Amino acid sequence Gl-2635=SEQ ID NO:3.

FIG. 3A illustrates fluorescence analysis of green fluorescent protein (GFP) infected A549.tTA control cells. FIG. 3B illustrates cell tracker assay data from GFP infected A549.tTA control cells. FIG. 3C illustrates fluorescence analysis of NP95 infected A549.tTA cells. FIG. 3D illustrates cell tracker assay date from NP95 infected A549.tTA cells.

DETAILED DESCRIPTION OF THE INVENTION

Introduction

Figure 3:
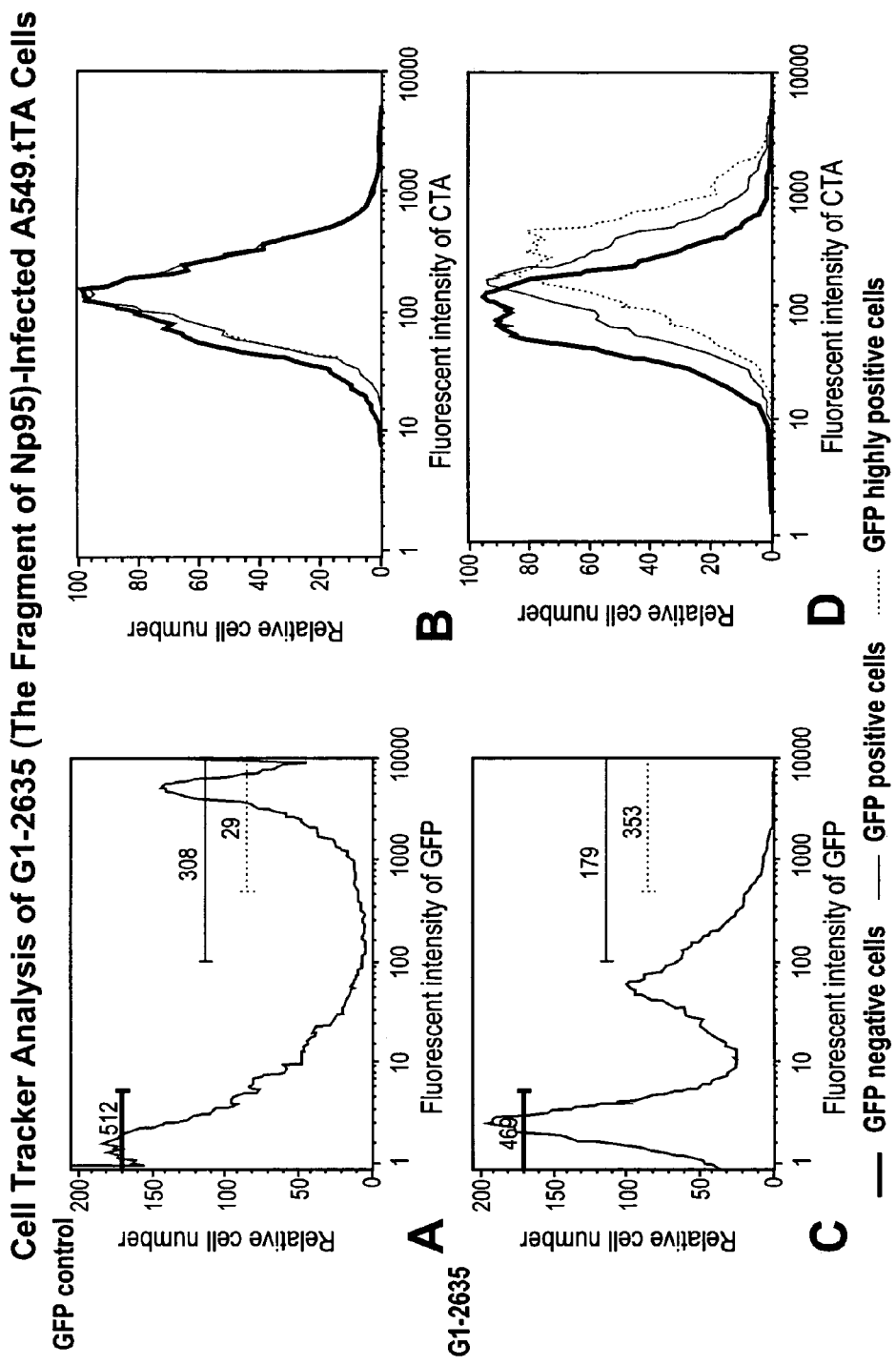
FIG. 3 illustrates cell tracker assay data demonstrating that GFP-fused NP95 is antiproliferative in A549.

The NP95 gene encodes a nuclear zinc finger protein which is associated with cellular proliferation (see, e.g., Fujimori et al. *Mammalian Genome* 9:1032–1035 (1998). The NP95 open reading frame contains a potential ATP/GTP binding site, a zinc finger motif, a putative cyclin A/E cdk2 phosphorylation site, and a retinoblastoma binding motif (see, e.g., Miura et al. *Exp. Cell Res.* 263:202–208 (2001). However, NP95 involvement in cellular transformation, tumorigenesis, and anti-proliferative effects in tumor cells has never been demonstrated. Furthermore, the role of NP95 in cell cycle regulation has not yet been elucidated.

As described below, the present inventors identified human NP95 in a cDNA library screening assay. As shown in FIG. 3, studies with NP95 show NP95 has a antiproliferative phenotype (using, e.g., GFP positivity and cell tracker assays). These functional studies, presented herein, demonstrate for the first time that inhibition of NP95 will inhibit tumor cell growth. With cellular staining of NP95 infected A549.tTA cells, fluorescence analysis shows that NP95 is localized to the nucleus of NP95 infected cells.

NP95 therefore represents a drug target for compounds that suppress or activate cellular proliferation in tumor cells, or cause cell cycle arrest, cause release from cell cycle arrest, activate apoptosis, increase sensitivity to chemotherapeutic (adjuvant) reagents, and decrease toxicity of chemotherapeutic reagents. Agents identified in these assays, including small organic molecules, peptides, cyclic peptides, nucleic acids, antibodies, antisense nucleic acids, RNAi, and ribozymes, that modulate cell cycle regulation and cellular proliferation via modulation of NP95, can be used to treat diseases related to cellular proliferation, such as cancer. In particular, inhibitors of NP95 are useful for inhibition of cancer and tumor cell growth. NP95 modulators can also be used to modulate the sensitivity of cells to chemotherapeutic agents, such as bleomycin, etoposide, taxol, and other agents known to those of skill in the art. NP95 modulators can also be used to decrease toxicity of such chemotherapeutic reagents.

In one embodiment, ubiquitin ligase assays using NP95 can be used to identify modulators of NP95 ubiquitin ligase activity, or to identify proteins that bind to NP95, e.g., NP95 substrates. Full length wild type NP95, mutant NP95, or the NP95 ubiquitin ligase domain can be used in these assays. Such assays can be performed in vitro, or can be cell-based (see, e.g., Example 3). A ubiquitin ligase substrate or a peptide having the ubiquitin ligase recognition site can used in such assays. Suitable controls and assays for ubiquitin ligase activity are known in the art (see, e.g., Weissman, *Nature Reviews* 2:169–178 (2001); Hass & Siepmann, *FASEB J.* 11:1257–1268 (1997); Huang et al., *Science* 286:1321–1326 (1999); King et al., *Science* 274:1652–1659 (1996); Hershko et al., *Ann Rev. Biochem.* 67:429–475 (1998); Koepp et al., *Cell* 97:431–434 (1999); Tan et al., *Mol. Cell.* 3:527–533 (1999); Laney et al., *Cell* 97:427–430 (1999) and Lorick et al., *Proc. Nat'l Acad. Sci. USA* 96:11364–11369 (1999)). In another embodiment, a substrate free, auto E3 ubiquitin ligase assay can be used (see, e.g., WO 01/75145).

Such modulators are useful for treating cancers, such as melanoma, breast, ovarian, lung, gastrointestinal and colon, prostate, and leukemia and lymphomas, e.g., multiple myeloma. In addition, such modulators are useful for treating noncancerous disease states caused by pathologically proliferating cells such as thyroid hyperplasia (Grave's disease), psoriasis, benign prostatic hypertrophy, neurofibromas, atherosclerosis, restenosis, and other vasoproliferative disease.

Definitions

By "disorder associated with cellular proliferation" or "disease associated with cellular proliferation" herein is meant a disease state which is marked by either an excess or a deficit of cellular proliferation or apoptosis. Such disorders associated with increased cellular proliferation include, but are not limited to, cancer and non-cancerous pathological proliferation.

The terms "NP95" or a nucleic acid encoding "NP95" refer to nucleic acids and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by an NP95 nucleic acid (for a human NP95 nucleic acid sequence, see, e.g., FIG. 1, SEQ ID NO:1, or Accession number AF274048 or amino acid sequence of an NP95 protein (for a human NP95 protein sequence, see, e.g., FIG. 1, SEQ ID NO:2 or Accession number AAK55744.1; (2) bind to antibodies, e.g., polyclonal antibodies, raised against an immunogen comprising an amino acid sequence of an NP95 protein, and conservatively modified variants thereof; (3) specifically hybridize under stringent hybridization conditions to an anti-sense strand corresponding to a nucleic acid sequence encoding an NP95 protein, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to an NP95 nucleic acid or a nucleic acid encoding the ubiquitin ligase domain. Preferably the ligase domain has greater than 96%, 97%, 98%, or 99% amino acid identity to the human NP95 ligase domain of SEQ ID NO:2. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. A NP95 protein typically has ubiquitin ligase activity. Ubiquitin ligase assays can be performed according to methods known to those of skill in the art, using substrates having a ubiquitin ligase recognition site.

The phrase "functional effects" in the context of assays for testing compounds that modulate activity of an NP95 protein includes the determination of a parameter that is indirectly or directly under the influence of an NP95, e.g., a phenotypic or chemical effect, such as the ability to increase or decrease cellular proliferation, apoptosis, cell cycle arrest, or ubiquitin ligase activity; or e.g., a physical effect such as ligand binding or inhibition of ligand binding. A functional effect therefore includes ligand binding activity, the ability of cells to proliferate, apoptosis, and enzyme activity. "Functional effects" include in vitro, in vivo, and ex vivo activities.

By "determining the functional effect" is meant assaying for a compound that increases or decreases a parameter that is indirectly or directly under the influence of an NP95 protein, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape); chromatographic; or solubility properties for the protein; measuring inducible markers or transcriptional activation of the protein; measuring binding activity or binding assays, e.g. binding to antibodies; measuring changes in ligand or substrate binding activity; measuring cellular proliferation; measuring cell morphology, e.g., spindle formation or chromosome formation; measuring phosphorylated proteins such as histone H3 using antibodies; measuring apoptosis; measuring cell surface marker expression; measurement of changes in protein levels for NP95-associated sequences; measurement of RNA stability; phosphorylation or dephosphorylation; ligase activity; identification of downstream or reporter gene expression (CAT, luciferase, β-gal, GFP and the like), e.g., via chemiluminescence, fluorescence, colorimetric reactions, antibody binding, and inducible markers.

"Inhibitors", "activators", and "modulators" of NP95 polynucleotide and polypeptide sequences are used to refer to activating, inhibitory, or modulating molecules identified using in vitro and in vivo assays of NP95 polynucleotide and polypeptide sequences. Inhibitors are compounds that, e.g., bind to, partially or totally block activity, decrease, prevent, delay activation, inactivate, desensitize, or down regulate the activity or expression of NP95 proteins, e.g., antagonists. "Activators" are compounds that increase, open, activate, facilitate, enhance activation, sensitize, agonize, or up regulate NP95 protein activity, e.g., agonists. Inhibitors, activators, or modulators also include genetically modified versions of NP95 proteins, e.g., versions with altered activity, as well as naturally occurring and synthetic ligands, antagonists, agonists, antibodies, peptides, cyclic peptides, nucleic acids, antisense molecules, ribozymes, small chemical molecules and the like. Such assays for inhibitors and activators include, e.g., expressing NP95 protein in vitro, in cells, or cell membranes, applying putative modulator compounds, and then determining the functional effects on activity, as described above.

Samples or assays comprising NP95 proteins that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of NP95 is achieved when the activity value relative to the control is about 80%, preferably 50%, more preferably 25-0%. Activation of NP95 is achieved when the activity value relative to the control (untreated with activators) is 110%, more preferably 150%, more preferably 200–500% (i.e., two to five fold higher relative to the control), more preferably 1000–3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulation tumor cell proliferation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence SEQ ID NO:1 or amino acid sequence SEQ ID NO:2), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52): 35095–35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I. The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity, e.g., a ligase domain. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5× SSC, and 1% SDS, incubating at 42° C., or, 5× SSC, 1% SDS, incubating at 65° C., with wash in 0.2× SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1× SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.–95° C. for 30 sec–2 min., an annealing phase lasting 30 sec.–2 min., and an extension phase of about 72° C. for 1–2 min. Protocols and guidelines for low and high stringency amplification reactions are provided, e.g., in Innis et al. (1990) PCR Protocols, A Guide to Methods and Applications, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552–554 (1990)).

For preparation of antibodies, e.g., recombinant, monoclonal, or polyclonal antibodies, many technique known in the art can be used (see, e.g., Kohler & Milstein, Nature 256:495–497 (1975); Kozbor et al., Immunology Today 4:72 (1983); Cole et al., pp. 77–96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779–783 (1992); Lonberg et al., Nature 368:856–859 (1994); Morrison, Nature 368:812–13 (1994); Fishwild et al., Nature Biotechnology 14:845–51 (1996); Neuberger, Nature Biotechnology 14:826 (1996); and Lonberg & Huszar, Intern. Rev. Immunol. 13:65–93 (1995)). Alternatively, phage display technology can be used to identify antibodies and heteromeric Fab fragments that specifically bind to selected antigens (see, e.g., McCafferty et al., Nature 348:552–554 (1990); Marks et al., Biotechnology 10:779–783 (1992)). Antibodies can also be made bispecific, i.e., able to recognize two different antigens (see, e.g., WO 93/08829, Traunecker et al., EMBO J. 10:3655–3659 (1991); and Suresh et al., Methods in Enzymology 121:210 (1986). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain.

Humanization can be essentially performed following the method of Winter and co-workers (see, e.g., Jones et al., *Nature* 321:522–525 (1986); Riechmann et al., *Nature* 332: 323–327 (1988); Verhoeyen et al., *Science* 239:1534–1536 (1988) and Presta, *Curr. Op. Struct. Biol.* 2:593–596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to a NP95 protein, polymorphic variants, alleles, orthologs, and conservatively modified variants, or splice variants, or portions thereof, can be selected to obtain only those polyclonal antibodies that are specifically immunoreactive with NP95 proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, *A Laboratory Manual* (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1–3, 1992); Lloyd, *The Art, Science and Technology of Pharmaceutical Compounding* (1999); and Pickar, *Dosage Calculations* (1999)).

Assays for Proteins that Modulation Cellular Proliferation

High throughput functional genomics assays can be used to identify modulators of cellular proliferation. Such assays can monitor changes in cell surface marker expression, proliferation and differentiation, and apoptosis, using either cell lines or primary cells. Typically, the cells are contacted with a cDNA or a random peptide library (encoded by nucleic acids). In one embodiment, the peptides are cyclic or circular. The cDNA library can comprise sense, antisense, full length, and truncated cDNAs. The peptide library is encoded by nucleic acids. The effect of the cDNA or peptide library on the phenotype of cellular proliferation is then monitored, using an assay as described above. The effect of the cDNA or peptide can be validated and distinguished from somatic mutations, using, e.g., regulatable expression of the nucleic acid such as expression from a tetracycline promoter. cDNAs and nucleic acids encoding peptides can be rescued using techniques known to those of skill in the art, e.g., using a sequence tag.

Proteins interacting with the peptide or with the protein encoded by the cDNA (e.g., NP95) can be isolated using a yeast two-hybrid system, mammalian two hybrid system, immunoprecipitation or affinity chromatography of complexed proteins followed by mass spectrometry, or phage display screen, etc. Targets so identified can be further used as bait in these assays to identify additional members of the cellular proliferation pathway, which members are also targets for drug development (see, e.g., Fields et al., *Nature* 340:245 (1989); Vasavada et al., *Proc. Nat'l Acad. Sci. USA* 88:10686 (1991); Fearon et al., *Proc. Nat'l Acad. Sci. USA* 89:7958 (1992); Dang et al., *Mol. Cell. Biol.* 11:954 (1991); Chien et al., *Proc. Nat'l Acad. Sci. USA* 9578 (1991); and U.S. Pat. Nos. 5,283,173, 5,667,973, 5,468,614, 5,525,490, and 5,637,463).

Suitable cell lines include A549, HeLa, Colo205, H1299, MCF7, MDA-MB-231, PC3, HMEC, PrEC. Cell surface markers can be assayed using fluorescently labeled antibodies and FACS. Cell proliferation can be measured using $^3$H-thymidine incorporation, cell count by dye inclusion, MTT assay, BrdU incorporation, Cell Tracker assay. Apoptosis can be measured using dye inclusion, or by assaying for DNA laddering, increases in intracellular calcium, or caspare activation. Growth factor production can be measured using an immunoassay such as ELISA.

cDNA libraries are made from any suitable source. Libraries encoding random peptides are made according to techniques well known to those of skill in the art (see, e.g., U.S. Pat. Nos. 6,153,380, 6,114,111, and 6,180,343). Any suitable vector can be used for the cDNA and peptide libraries, including, e.g., retroviral vectors.

Isolation of Nucleic Acids encoding NP95 Family Members

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

NP95 nucleic acids, polymorphic variants, orthologs, and alleles that are substantially identical to an amino acid sequence encoded by SEQ ID NO:2 can be isolated using NP95 nucleic acid probes and oligonucleotides under stringent hybridization conditions, by screening libraries. Alternatively, expression libraries can be used to clone NP95 protein, polymorphic variants, orthologs, and alleles by detecting expressed homologs immunologically with antisera or purified antibodies made against human NP95 or portions thereof.

To make a cDNA library, one should choose a source that is rich in NP95 RNA. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA*, 72:3961–3965 (1975).

An alternative method of isolating NP95 nucleic acid and its orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of human NP95 directly from mRNA, from cDNA, from genomic libraries or cDNA libraries. Degenerate oligonucleotides can be designed to amplify NP95 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of NP95 encoding mRNA in physiological samples, for nucleic acid sequencing, or for other purposes. Genes amplified by the PCR reaction can be purified from agarose gels and cloned into an appropriate vector.

Gene expression of NP95 can also be analyzed by techniques known in the art, e.g., reverse transcription and amplification of mRNA, isolation of total RNA or poly $A^+$ RNA, northern blotting, dot blotting, in situ hybridization, RNase protection, high density polynucleotide array technology, e.g., and the like.

Nucleic acids encoding NP95 protein can be used with high density oligonucleotide array technology (e.g., GeneChip™) to identify NP95 protein, orthologs, alleles, conservatively modified variants, and polymorphic variants in this invention. In the case where the homologs being identified are linked to modulation of cellular proliferation, they can be used with GeneChip™ as a diagnostic tool in detecting the disease in a biological sample, see, e.g., Gunthand et al., *AIDS Res. Hum. Retroviruses* 14:869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

The gene for NP95 is typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Euaryotes

To obtain high level expression of a cloned gene, such as those cDNAs encoding NP95, one typically subclones NP95 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the NP95 protein are available in, e.g., *E. coli*, *Bacillus* sp., and *Salmonella* (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available. In one preferred embodiment, retroviral expression systems are used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the NP95 encoding nucleic acid in host cells. A typical expression cassette thus contains a promoter operably linked to the nucleic acid sequence encoding NP95 and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/$A^+$, pMTO10/$A^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention have a regulatable promoter, e.g., tet-regulated systems and the RU-486 system (see, e.g., Gossen & Bujard, *PNAS* 89:5547 (1992); Oligino et al., *Gene Ther.* 5:491–496 (1998); Wang et al., *Gene Ther.* 4:432–441 (1997); Neering et al., *Blood* 88:1147–1155 (1996); and Rendahl et al., *Nat. Biotechnol.* 16:757–761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a NP95 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of NP95 protein, which are then purified using standard techniques (see, e.g., Colley et al., *J. Biol. Chem.* 264:17619–17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing NP95.

After the expression vector is introduced into the cells, the transfected cells are cultured under conditions favoring expression of NP95, which is recovered from the culture using standard techniques identified below.

Purification of NP95 Polypeptides

Either naturally occurring or recombinant NP95 can be purified for use in functional assays. Naturally occurring NP95 can be purified, e.g., from human tissue. Recombinant NP95 can be purified from any suitable expression system.

The NP95 protein may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant NP95 protein is being purified. For example, proteins having established molecular adhesion properties can be reversible fused to the NP95 protein. With the appropriate ligand or substrate, e.g., antiphospho S/T antibodies or anti-NP95 antibodies, NP95 protein can be selectively adsorbed to a purification column and then freed from the column in a relatively pure form. The fused protein is then removed by enzymatic activity. Finally, NP95 protein could be purified using immunoaffinity columns. Recombinant NP95 protein can be purified from any suitable source, include yeast, insect, bacterial, and mammalian cells.

A. Purification of NP95 from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of NP95 protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein.

Other suitable buffers are known to those skilled in the art. Human NP95 proteins are separated from other bacterial proteins by standard separation techniques, e.g., with Ni-NTA agarose resin.

Alternatively, it is possible to purify NP95 protein from bacteria periplasm. After lysis of the bacteria, when the NP95 protein exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying NP95 Proteins

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the NP95 proteins can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The NP95 proteins can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Assays for Modulators of NP95 Protein

A. Assays

Modulation of an NP95 protein, and corresponding modulation of cellular, e.g., tumor cell, proliferation, can be assessed using a variety of in vitro and in vivo assays, including cell-based models. Such assays can be used to test for inhibitors and activators of NP95 protein, and, consequently, inhibitors and activators of cellular proliferation, including modulators of chemotherapeutic sensitivity and toxicity. Such modulators of NP95 protein are useful for treating disorders related to pathological cell proliferation, e.g., cancer. Modulators of NP95 protein are tested using either recombinant or naturally occurring NP95, preferably human NP95.

Preferably, the NP95 protein will have the sequence as encoded by SEQ ID NO:2 or a conservatively modified variant thereof. Alternatively, the NP95 protein of the assay will be derived from a eukaryote and include an amino acid subsequence having substantial amino acid sequence identity to SEQ ID NO:2. Generally, the amino acid sequence identity will be at least 60%, preferably at least 65%, 70%, 75%, 80%, 85%, or 90%, most preferably at least 95%.

Measurement of cellular proliferation modulation with NP95 protein or a cell expressing NP95 protein, either recombinant or naturally occurring, can be performed using a variety of assays, in vitro, in vivo, and ex vivo, as described herein. A suitable physical, chemical or phenotypic change that affects activity, e.g., enzymatic activity such as ligase activity, cell proliferation, or ligand binding can be used to assess the influence of a test compound on the polypeptide of this invention. When the functional effects are determined using intact cells or animals, one can also measure a variety of effects, such as, ligand binding, ligase activity, transcriptional changes to both known and uncharacterized genetic markers (e.g., northern blots), changes in cell metabolism, changes related to cellular proliferation, cell surface marker expression, DNA synthesis, marker and dye dilution assays (e.g., GFP and cell tracker assays), contact inhibition, tumor growth in nude mice, etc.

In Vitro Assays

Assays to identify compounds with NP95 modulating activity can be performed in vitro. Such assays can used full length NP95 protein or a variant thereof (see, e.g., SEQ ID NO:2), or a mutant thereof, or a fragment of an NP95 protein, such as a ligase domain. Purified recombinant or naturally occurring NP95 protein can be used in the in vitro methods of the invention. In addition to purified NP95 protein, the recombinant or naturally occurring NP95 protein can be part of a cellular lysate or a cell membrane. As described below, the binding assay can be either solid state or soluble. Preferably, the protein or membrane is bound to a solid support, either covalently or non-covalently. Often, the in vitro assays of the invention are substrate or ligand binding or affinity assays, either non-competitive or competitive (with a ligand of ubiquitin ligase or a substrate having a ubiquitin ligase site). Other in vitro assays include measuring changes in spectroscopic (e.g., fluorescence, absorbance, refractive index), hydrodynamic (e.g., shape), chromatographic, or solubility properties for the protein. Other in vitro assays include enzymatic activity assays.

In one embodiment, a high throughput binding assay is performed in which the NP95 protein or a fragment thereof is contacted with a potential modulator and incubated for a suitable amount of time. In one embodiment, the potential modulator is bound to a solid support, and the NP95 protein is added. In another embodiment, the NP95 protein is bound to a solid support. A wide variety of modulators can be used, as described below, including small organic molecules, peptides, antibodies, and NP95 ligand analogs. A wide variety of assays can be used to identify NP95-modulator binding, including labeled protein-protein binding assays, electrophoretic mobility shifts, immunoassays, enzymatic assays such as ligase assays, and the like. In some cases, the binding of the candidate modulator is determined through the use of competitive binding assays, where interference with binding of a known ligand or substrate is measured in the presence of a potential modulator. Either the modulator or the known ligand or substrate is bound first, and then the competitor is added. After the NP95 protein is washed, interference with binding, either of the potential modulator or of the known ligand or substrate, is determined. Often, either the potential modulator or the known ligand or substrate is labeled.

Cell-Based In Vivo Assays

In another embodiment, NP95 protein is expressed in a cell, and functional, e.g., physical and chemical or phenotypic, changes are assayed to identify NP95 and modulators of cellular proliferation, e.g., tumor cell proliferation. Cells expressing NP95 proteins can also be used in binding assays and enzymatic assays. Any suitable functional effect can be measured, as described herein. For example, cellular morphology (e.g., cell volume, nuclear volume, cell perimeter, and nuclear perimeter), ligand binding, ligase activity, apoptosis, cell surface marker expression, cellular proliferation, GFP positivity and dye dilution assays (e.g., cell tracker assays with dyes that bind to cell membranes), DNA synthesis assays (e.g., $^3$H-thymidine and fluorescent DNA-binding dyes such as BrdU or Hoescht dye with FACS analysis), are all suitable assays to identify potential modulators using a cell based system. Suitable cells for such cell based assays include both primary cancer or tumor cells and cell lines, as described herein, e.g., A549 (lung), MCF7 (breast, p53 wild-type), H1299 (lung, p53 null), Hela (cervical), PC3 (prostate, p53 mutant), MDA-MB-231 (breast, p53 wild-type). Cancer cell lines can be p53 mutant, p53 null, or express wild type p53. The NP95 protein can be naturally occurring or recombinant. Also, fragments of NP95 or chimeric NP95 proteins with ligase activity can be used in cell based assays.

Cellular NP95 polypeptide levels can be determined by measuring the level of protein or mRNA. The level of NP95 protein or proteins related to NP95 are measured using immunoassays such as western blotting, ELISA and the like with an antibody that selectively binds to the NP95 polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, NP95 expression can be measured using a reporter gene system. Such a system can be devised using an NP95 protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g., Mistili & Spector, *Nature Biotechnology* 15:961–964 (1997)). The reporter construct is typically transfected into a cell. After treatment with a potential modulator, the amount of reporter gene transcription, translation, or activity is measured according to standard techniques known to those of skill in the art.

Animal Models

Animal models of cellular proliferation also find use in screening for modulators of cellular proliferation. Similarly, transgenic animal technology including gene knockout technology, for example as a result of homologous recombination with an appropriate gene targeting vector, or gene overexpression, will result in the absence or increased expression of the NP95 protein. The same technology can also be applied to make knock-out cells. When desired, tissue-specific expression or knockout of the NP95 protein may be necessary. Transgenic animals generated by such methods find use as animal models of cellular proliferation and are additionally useful in screening for modulators of cellular proliferation.

Knock-out cells and transgenic mice can be made by insertion of a marker gene or other heterologous gene into an endogenous NP95 gene site in the mouse genome via homologous recombination. Such mice can also be made by substituting an endogenous NP95 with a mutated version of the NP95 gene, or by mutating an endogenous NP95, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

Exemplary Assays

Ligase Activity Assays—In Vitro or Cell Based

In one embodiment, ligase assays using NP95 can be used to identify modulators of NP95 ligase activity, or to identify proteins that bind to NP95, e.g., NP95 substrates. Full length wild type NP95, mutant NP95, or the NP95 ligase domain can be used in these assays. Such assays can be performed in vitro, using recombinant NP95 or cellular lysates comprising endogenous or recombinant NP95, or can be cell-based. A ubiquitin ligase substrate or a peptide having a ubiquitin ligase recognition site can be used in such assays.

Soft Agar Growth or Colony Formation in Suspension

Normal cells require a solid substrate to attach and grow. When the cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, regenerate normal phenotype and require a solid substrate to attach and grow.

Soft agar growth or colony formation in suspension assays can be used to identify NP95 modulators. Typically, transformed host cells (e.g., cells that grow on soft agar) are used in this assay. For example, RKO or HCT116 cell lines can be used. Techniques for soft agar growth or colony formation in suspension assays are described in Freshney,

*Culture of Animal Cells a Manual of Basic Technique*, 3rd ed., Wiley-Liss, New York (1994), herein incorporated by reference. See also, the methods section of Garkavtsev et al. (1996), supra, herein incorporated by reference.

Contact Inhibition and Density Limitation of Growth

Normal cells typically grow in a flat and organized pattern in a petri dish until they touch other cells. When the cells touch one another, they are contact inhibited and stop growing. When cells are transformed, however, the cells are not contact inhibited and continue to grow to high densities in disorganized foci. Thus, the transformed cells grow to a higher saturation density than normal cells. This can be detected morphologically by the formation of a disoriented monolayer of cells or rounded cells in foci within the regular pattern of normal surrounding cells. Alternatively, labeling index with [$^3$H]-thymidine at saturation density can be used to measure density limitation of growth. See Freshney (1994), supra. The transformed cells, when contacted with cellular proliferation modulators, regenerate a normal phenotype and become contact inhibited and would grow to a lower density.

Contact inhibition and density limitation of growth assays can be used to identify NP95 modulators which are capable of inhibiting abnormal proliferation and transformation in host cells. Typically, transformed host cells (e.g., cells that are not contact inhibited) are used in this assay. For example, RKO or HCT116 cell lines can be used. In this assay, labeling index with [$^3$H]-thymidine at saturation density is a preferred method of measuring density limitation of growth. Transformed host cells are contacted with a potential NP95 modulator and are grown for 24 hours at saturation density in non-limiting medium conditions. The percentage of cells labeling with [$^3$H]-thymidine is determined autoradiographically. See, Freshney (1994), supra. The host cells contacted with a NP95 modulator would give arise to a lower labeling index compared to control (e.g., transformed host cells transfected with a vector lacking an insert).

Growth Factor or Serum Dependence

Growth factor or serum dependence can be used as an assay to identify NP95 modulators. Transformed cells have a lower serum dependence than their normal counterparts (see, e.g., Temin, *J. Natl. Cancer Insti.* 37:167–175 (1966); Eagle et al., *J. Exp. Med.* 131:836–879 (1970)); Freshney, supra. This is in part due to release of various growth factors by the transformed cells. When transformed cells are contacted with a NP95 modulator, the cells would reacquire serum dependence and would release growth factors at a lower level.

Tumor Specific Markers Levels

Tumor cells release an increased amount of certain factors (hereinafter "tumor specific markers") than their normal counterparts. For example, plasminogen activator (PA) is released from human glioma at a higher level than from normal brain cells (see, e.g., Gullino, *Angiogenesis, tumor vascularization, and potential interference with tumor growth*. In Mibich (ed.): "Biological Responses in Cancer." New York, Academic Press, pp. 178–184 (1985)). Similarly, tumor angiogenesis factor (TAF) is released at a higher level in tumor cells than their normal counterparts. See, e.g., Folkman, Angiogenesis and cancer, *Sem Cancer Biol.* (1992)).

Tumor specific markers can be assayed to identify NP95 modulators which decrease the level of release of these markers from host cells. Typically, transformed or tumorigenic host cells are used. Various techniques which measure the release of these factors are described in Freshney (1994), supra. Also, see, Unkless et al., *J. Biol. Chem.* 249:4295–4305 (1974); Strickland & Beers, *J. Biol. Chem.* 251:5694–5702 (1976); Whur et al., *Br. J. Cancer* 42:305–312 (1980); Gulino, *Angiogenesis, tumor vascularization, and potential interference with tumor growth*. In Mihich, E. (ed): "Biological Responses in Cancer." New York, Plenum (1985); Freshney *Anticancer Res.* 5:111–130 (1985).

Invasiveness Into Matrigel

The degree of invasiveness into Matrigel or some other extracellular matrix constituent can be used as an assay to identify NP95 modulators which are capable of inhibiting abnormal cell proliferation and tumor growth. Tumor cells exhibit a good correlation between malignancy and invasiveness of cells into Matrigel or some other extracellular matrix constituent. In this assay, tumorigenic cells are typically used as host cells. Therefore, NP95 modulators can be identified by measuring changes in the level of invasiveness between the host cells before and after the introduction of potential modulators. If a compound modulates NP95, its expression in tumorigenic host cells would affect invasiveness.

Techniques described in Freshney (1994), supra, can be used. Briefly, the level of invasion of host cells can be measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$I and counting the radioactivity on the distal side of the filter or bottom of the dish. See, e.g., Freshney (1984), supra.

Apoptosis Analysis

Apoptosis analysis can be used as an assay to identify NP95 modulators. In this assay, cell lines, such as RKO or HCT116, can be used to screen NP95 modulators. Cells are contacted with a putative NP95 modulator. The cells can be co-transfected with a construct comprising a marker gene, such as a gene that encodes green fluorescent protein, or a cell tracker dye. The apoptotic change can be determined using methods known in the art, such as DAPI staining and TUNEL assay using fluorescent microscope. For TUNEL assay, commercially available kit can be used (e.g., Fluorescein FragEL DNA Fragmentation Detection Kit (Oncogene Research Products, Cat. #QIA39)+Tetramethylrhodamine-5-dUTP (Roche, Cat. #1534 378)). Cells contacted with NP95 modulators would exhibit, e.g., an increased apoptosis compared to control.

$G_0/G_1$ Cell Cycle Arrest Analysis $G_0/G_1$ cell cycle arrest can be used as an assay to identify NP95 modulators. In this assay, cell lines, such as RKO or HCT116, can be used to screen NP95 modulators. The cells can be co-transfected with a construct comprising a marker gene, such as a gene that encodes green fluorescent protein, or a cell tracker dye. Methods known in the art can be used to measure the degree of $G_1$ cell cycle arrest. For example, a propidium iodide signal can be used as a measure for DNA content to determine cell cycle profiles on a flow cytometer. The percent of the cells in each cell cycle can be calculated. Cells contacted with a NP95 modulator would exhibit, e.g., a higher number of cells that are arrested in $G_0/G_1$ phase compared to control.

Tumor Growth In Vivo

Effects of NP95 modulators on cell growth can be tested in transgenic or immune-suppressed mice. Knock-out transgenic mice can be made, in which the endogenous NP95 gene is disrupted. Such knock-out mice can be used to study effects of NP95, e.g., as a cancer model, as a means of assaying in vivo for compounds that modulate NP95, and to test the effects of restoring a wild-type or mutant NP95 to a knock-out mice.

Knock-out cells and transgenic mice can be made by insertion of a marker gene or other heterologous gene into the endogenous NP95 gene site in the mouse genome via homologous recombination. Such mice can also be made by substituting the endogenous NP95 with a mutated version of NP95, or by mutating the endogenous NP95, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987). These knock-out mice can be used as hosts to test the effects of various NP95 modulators on cell growth.

Alternatively, various immune-suppressed or immune-deficient host animals can be used. For example, genetically athymic "nude" mouse (see, e.g., Giovanella et al., *J. Natl. Cancer Inst.* 52:921 (1974)), a SCID mouse, a thymectomized mouse, or an irradiated mouse (see, e.g., Bradley et al., *Br. J. Cancer* 38:263 (1978); Selby et al., *Br. J. Cancer* 41:52 (1980)) can be used as a host. Transplantable tumor cells (typically about $10^6$ cells) injected into isogenic hosts will produce invasive tumors in a high proportions of cases, while normal cells of similar origin will not. Hosts are treated with NP95 modulators, e.g., by injection. After a suitable length of time, preferably 4–8 weeks, tumor growth is measured (e.g., by volume or by its two largest dimensions) and compared to the control. Tumors that have statistically significant reduction (using, e.g., Student's T test) are said to have inhibited growth. Using reduction of tumor size as an assay, NP95 modulators which are capable, e.g., of inhibiting abnormal cell proliferation can be identified.

B. Modulators

The compounds tested as modulators of NP95 protein can be any small organic molecule, or a biological entity, such as a protein, e.g., an antibody or peptide, a sugar, a nucleic acid, e.g., an antisense oligonucleotide or a ribozyme, or a lipid. Alternatively, modulators can be genetically altered versions of an NP95 protein. Typically, test compounds will be small organic molecules, peptides, circular peptides, RNAi, antisense molecules, ribozymes, and lipids.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274: 1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., Chem-Star, Ltd, Moscow, RU, 3D Pharmaceuticals, Exton, Pa., Martek Biosciences, Columbia, Md., etc.).

C. Solid State and Soluble High Throughput Assays

In one embodiment the invention provides soluble assays using a NP95 protein, or a cell or tissue expressing an NP95 protein, either naturally occurring or recombinant. In another embodiment, the invention provides solid phase based in vitro assays in a high throughput format, where the NP95 protein or NP95 substrate is attached to a solid phase. Any one of the assays described herein can be adapted for high throughput screening.

In the high throughput assays of the invention, either soluble or solid state, it is possible to screen up to several thousand different modulators or ligands in a single day. This methodology can be used for NP95 proteins in vitro, or for cell-based or membrane-based assays comprising an NP95 protein. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100–about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage. A tag for covalent or non-covalent binding can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly Gly sequences of between about 5 and 200 amino acids (SEQ ID NO:3). Such flexible linkers are known to persons of skill in the art. For example, poly (ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767–777 (1991); Sheldon et al., *Clinical Chemistry* 39(4):718–719 (1993); and Kozal et al., *Nature Medicine* 2(7):753759 (1996)(all describing arrays of biopolymers fixed to solid substrates). Non-chemical approaches for fixing tag binders to substrates include other common methods, such as heat, cross-linking by UV radiation, and the like.

Immunological Detection of NP95 Polypeptides

In addition to the detection of NP95 gene and gene expression using nucleic acid hybridization technology, one can also use immunoassays to detect NP95 proteins of the invention. Such assays are useful for screening for modulators of NP95, as well as for therapeutic and diagnostic applications. Immunoassays can be used to qualitatively or quantitatively analyze NP95 protein. A general overview of the applicable technology can be found in Harlow & Lane, *Antibodies: A Laboratory Manual* (1988).

A. Production of Antibodies

Methods of producing polyclonal and monoclonal antibodies that react specifically with the NP95 proteins are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of immunogens comprising portions of NP95 protein may be used to produce antibodies specifically reactive with NP95 protein. For example, recombinant NP95 protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-NP95 proteins, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a particular NP95 ortholog, such as human NP95, can also be made, by subtracting out other cross-reacting orthologs from a species such as a non-human mammal. In this manner, antibodies that bind only to NP95 protein may be obtained.

Once the specific antibodies against NP95 protein are available, the protein can be detected by a variety of immunoassay methods. In addition, the antibody can be used therapeutically as a NP95 modulators. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

NP95 protein can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the NP95 protein or antigenic subsequence thereof). The antibody (e.g., anti-NP95) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled NP95 or a labeled anti-NP95 antibody. Alternatively, the labeling agent may be a third moiety, such a secondary antibody, that specifically binds to the antibody/NP95 complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting NP95 in samples may be either competitive or noncompetitive. Noncompetitive immunoassays are assays in which the amount of antigen is directly measured. In one preferred "sandwich" assay, for example, the anti-NP95 antibodies can be bound directly to a solid substrate on which they are immobilized. These immobilized antibodies then capture NP95 present in the test sample. NP95 proteins thus immobilized are then bound by a labeling agent, such as a second NP95 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of NP95 protein present in the sample is measured indirectly by measuring the amount of a known, added (exogenous) NP95 protein displaced (competed away) from an anti-NP95 antibody by the unknown NP95 protein present in a sample. In one competitive assay, a known amount of NP95 protein is added to a sample and the sample is then contacted with an antibody that specifically binds to NP95 protein. The amount of exogenous NP95 protein bound to the antibody is inversely proportional to the concentration of NP95 protein present in the sample. In a particularly preferred embodiment, the antibody is immobilized on a solid substrate. The amount of NP95 protein bound to the antibody may be determined either by measuring the amount of NP95 present in NP95 protein/antibody complex, or alternatively by measuring the amount of remaining uncomplexed protein. The amount of NP95 protein may be detected by providing a labeled NP95 molecule.

A hapten inhibition assay is another preferred competitive assay. In this assay the known NP95 protein is immobilized on a solid substrate. A known amount of anti-NP95 antibody is added to the sample, and the sample is then contacted with the immobilized NP95. The amount of anti-NP95 antibody bound to the known immobilized NP95 is inversely proportional to the amount of NP95 protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Imunoassays in the competitive binding format can also be used for crossreactivity determinations. For example, an NP95 protein can be immobilized to a solid support. Proteins (e.g., NP95 and homologs) are added to the assay that compete for binding of the antisera to the immobilized antigen. The ability of the added proteins to compete for binding of the antisera to the immobilized protein is compared to the ability of the NP95 protein to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of an NP95 protein, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the NP95 protein that is required to inhibit 50% of binding, then the second protein is said to specifically bind to the polyclonal antibodies generated to NP95 immunogen.

Other Assay Formats

Western blot (immunoblot) analysis is used to detect and quantify the presence of NP95 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind NP95. The anti-NP 95 antibodies specifically bind to the NP95 on the solid support. These antibodies may be directly labeled or alternatively may be subsequently detected using labeled antibodies (e.g., labeled sheep anti-mouse antibodies) that specifically bind to the anti-NP95 antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize NP95 protein, or secondary antibodies that recognize anti-NP95.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Cellular Transfection and Gene Therapy

The present invention provides the nucleic acids of NP95 protein for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses a NP95 protein of the present invention, thereby mitigating the effects of absent, partial inactivation, or abnormal expression of an NP95 gene, particularly as it relates to cellular proliferation. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808–813 (1992); Nabel & Felgner, TIBTECH 11:211–217 (1993); Mitani & Caskey, TIBTECH 11:162–166 (1993); Mulligan, *Science* 926–932 (1993); Dillon, TIBTECH 11:167–175 (1993); Miller, *Nature* 357: 455–460 (1992); Van Brunt, *Biotechnology* 6(10):1149–1154 (1998); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* (Doerfler & Bohm eds., 1995); and Yu et al., *Gene Therapy* 1:13–26 (1994)).

Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, $17^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the NP95 protein, the physician evaluates circulating plasma levels of the vector, vector toxicities, progression of the disease, and the production of anti-vector antibodies. In general, the dose equivalent of a naked nucleic acid from a vector is from about 1 μg to 100 μg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

EXAMPLES

The following examples are offered to illustrate, but not to limit the claimed invention.

Example 1

Isolation of Genes Which Cause Cell Cycle Arrest

A GFP C-terminal cDNA fusion library with a tetOff inducible gene expression system was constructed using standard techniques known to those of skill in the art. Clones from the library were used to transfect A549 cells. Transfected cells were then stained with cell tracker dyes to monitor the cell cycle. Cells that stained more brightly with cells tracker dyes were identified as cell cycle arrested cells. Cycling cells were eliminated by transfection with a retrovirus encoding the diphtheria toxin alpha chain. Cycling cells are susceptible to retroviral infection, but cell cycle arrested cells are not. Cell tracker positive cells i.e., cell cycle arrested cells, were sorted into 96 well plates and expanded with doxycycline (Dox) treatment. AlamarBlue, an oxidation-reduction indicator, was used to evaluate the proliferative effect of Dox on individual clones. AlamarBlue exhibits a spectrophotometrically measurable shift in color when reduced, e.g., within a proliferating cell. Clones that failed to proliferate in the presence of Dox were identified as clones encoding genes that had antiproliferative effects. The gene or gene fragment of interest was then amplified by RT-PCR.

Example 2

Identification of NP95 as an Antiproliferative Protein

A549 cells were transfected with a clone containing a fragment of NP95. The transfected cells were stained with a cell cycle tracker dye. The NP95 transfected cells stained brightly with the cell cycle tracker dye, indicating that they were cell cycle arrested cells. Thus, NP95 was identified as an antiproliferative protein.

Example 3

Assay for Ubiquitin Ligase Activity

Assays for ubiquitin ligase activity were performed as described in (see, e.g., WO 01/75145.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A method for identifying a compound that modulates cell cycle arrest, the method comprising the steps of:
   (i) contacting a cell comprising an NP95 polypeptide with the compound, wherein the NP95 polypeptide comprises an amino acid sequence with at least 90% identity to SEQ ID NO:2, wherein the NP95 protein has ubiquitin ligase activity; and
   (ii) determining the chemical or phenotypic effect of the compound upon the cell comprising the NP95 polypeptide, thereby identifying a compound that modulates cell cycle arrest.

2. The method of claim 1, wherein the chemical or phenotypic effect is determined by measuring ubiquitin ligase activity of the NP95 polypeptide.

3. The method of claim 1, wherein the chemical or phenotypic effect is determined by measuring cellular proliferation.

4. The method of claim 3, wherein the cell cycle arrest is measured by assaying DNA synthesis or fluorescent marker level.

5. The method of claim 4, wherein DNA synthesis is measured by 3H thymidine incorporation, BrdU incorporation, or Hoescht staining.

6. The method of claim 4, wherein the fluorescent marker is selected from the group consisting of a cell tracker dye or green fluorescent protein.

7. The method of claim 1, wherein modulation is activation of cell cycle arrest.

8. The method of claim 1, wherein modulation is activation of cancer cell cycle arrest.

9. The method of claim 1, wherein the cell is a cancer cell.

10. The method of claim 9, wherein the cancer cell is a breast, prostate, colon, or lung cancer cell.

11. The method of claim 9, wherein the cancer cell is a transformed cell line.

12. The method of claim 11, wherein the transformed cell line is PC3, H1299, MDA-MB-231, MCF7, A549, or HeLa.

13. The method of claim 9, wherein the cancer cell is p53 null or mutant.

14. The method of claim 9, wherein the cancer cell is p53 wild-type.

15. The method of claim 1, wherein the NP95 polypeptide is recombinant.

16. The method of claim 1, wherein the NP95 polypeptide is encoded by a nucleic acid comprising a sequence of SEQ ID NO:1.

17. The method of claim 1, wherein the compound is an antibody.

18. The method of claim 1, wherein the compound is an antisense molecule.

19. The method of claim 1, wherein the compound is an RNAi molecule.

20. The method of claim 1, wherein the compound is a small organic molecule.

21. The method of claim 1, wherein the compound is a peptide.

22. The method of claim 21, wherein the peptide is circular.

23. A method for identifying a compound that modulates cell cycle arrest, the method comprising the steps of:
   (i) contacting the compound with an NP95 polypeptide, wherein the NP95 polypeptide comprises an amino acid sequence with at least 90% identity to SEQ ID NO:2, wherein the NP95 protein has ubiquitin ligase activity;
   (ii) determining the physical effect of the compound upon the NP95 polypeptide; and
   (iii) determining the chemical or phenotypic effect of the compound upon a cell comprising an NP95 polypeptide, thereby identifying a compound that modulates cell cycle arrest.

24. The method of claim 1 or claim 23, wherein the NP95 polypeptide comprises an amino acid sequence with at least 95% identity to SEQ ID NO:2.

25. The method of claim 24, wherein the NP95 polypeptide comprises SEQ ID NO:2.

* * * * *

SEQUENCE LISTING

```
<160> NUMBER OF SEQ ID NOS: 4

<210> SEQ ID NO 1
<211> LENGTH: 3828
<212> TYPE: DNA
<213> ORGANISM: Homo sapiens
<220> FEATURE:
<223> OTHER INFORMATION: human NP95 nuclear zinc finger protein
<220> FEATURE:
<221> NAME/KEY: CDS
<222> LOCATION: (85)..(2466)
<223> OTHER INFORMATION: NP95

<400> SEQUENCE: 1
cgactcctta gagcatggca tggctcagag gtgctggtaa aactgatggg ggtttttgct      60
gtccctcccc tcagcgccga cacc atg tgg atc cag gtt cgg acc atg gac         111
                         Met Trp Ile Gln Val Arg Thr Met Asp
                          1               5 ggg agg cag acc cac acg gtg gac tcg ctg tcc agg ctg acc aag gtg        159
Gly Arg Gln Thr His Thr Val Asp Ser Leu Ser Arg Leu Thr Lys Val
 10                  15                  20                  25 gag gag ctg agg cgg aag atc cag gag ctg ttc cac gtg gag cca ggc        207
```

```
                Glu Glu Leu Arg Arg Lys Ile Gln Glu Leu Phe His Val Glu Pro Gly
                             30                  35                  40 ctg cag agg ctg ttc tac agg ggc aaa cag atg gag gac ggc cat acc            255
Leu Gln Arg Leu Phe Tyr Arg Gly Lys Gln Met Glu Asp Gly His Thr
             45                  50                  55 ctc ttc gac tac gag gtc cgc ctg aat gac acc atc cag ctc ctg gtc            303
Leu Phe Asp Tyr Glu Val Arg Leu Asn Asp Thr Ile Gln Leu Leu Val
         60                  65                  70 cgc cag agc ctc gtg ctc ccc cac agc acc aag gag cgg gac tcc gag            351
Arg Gln Ser Leu Val Leu Pro His Ser Thr Lys Glu Arg Asp Ser Glu
     75                  80                  85 ctc tcc gac acc gac tcc ggc tgc tgc ctg ggc cag agt gag tca gac            399
Leu Ser Asp Thr Asp Ser Gly Cys Cys Leu Gly Gln Ser Glu Ser Asp
 90                  95                 100                 105 aag tcc tcc acc cac ggc gag gcg gcc gcc gag act gac agc agg cca            447
Lys Ser Ser Thr His Gly Glu Ala Ala Ala Glu Thr Asp Ser Arg Pro
                 110                 115                 120 gcc gat gag gac atg tgg gat gag acg gaa ttg ggg ctg tac aag gtc            495
Ala Asp Glu Asp Met Trp Asp Glu Thr Glu Leu Gly Leu Tyr Lys Val
             125                 130                 135 aat gag tac gtc gat gct cgg gac acg aac atg ggg gcg tgg ttt gag            543
Asn Glu Tyr Val Asp Ala Arg Asp Thr Asn Met Gly Ala Trp Phe Glu
         140                 145                 150 gcg cag gtg gtc agg gtg acg cgg aag gcc ccc tcc cgg gac gag ccc            591
Ala Gln Val Val Arg Val Thr Arg Lys Ala Pro Ser Arg Asp Glu Pro
     155                 160                 165 tgc agc tcc acg tcc agg ccg gcg ctg gag gag gac gtc att tac cac            639
Cys Ser Ser Thr Ser Arg Pro Ala Leu Glu Glu Asp Val Ile Tyr His
170                 175                 180                 185 gtg aaa tac gac gac tac ccg gag aac ggc gtg gtc cag atg aac tcc            687
Val Lys Tyr Asp Asp Tyr Pro Glu Asn Gly Val Val Gln Met Asn Ser
                 190                 195                 200 agg gac gtc cga gcg cgc gcc cgc acc atc atc aag tgg cag gac ctg            735
Arg Asp Val Arg Ala Arg Ala Arg Thr Ile Ile Lys Trp Gln Asp Leu
             205                 210                 215 gag gtg ggc cag gtg gtc atg ctc aac tac aac ccc gac aac ccc aag            783
Glu Val Gly Gln Val Val Met Leu Asn Tyr Asn Pro Asp Asn Pro Lys
         220                 225                 230 gag cgg ggc ttc tgg tac gac gcg gag atc tcc agg aag cgc gag acc            831
Glu Arg Gly Phe Trp Tyr Asp Ala Glu Ile Ser Arg Lys Arg Glu Thr
     235                 240                 245 agg acg gcg cgg gaa ctc tac gcc aac gtg gtg ctg ggg gat gat tct            879
Arg Thr Ala Arg Glu Leu Tyr Ala Asn Val Val Leu Gly Asp Asp Ser
250                 255                 260                 265 ctg aac gac tgt cgg atc atc ttc gtg gac gaa gtc ttc aag att gag            927
Leu Asn Asp Cys Arg Ile Ile Phe Val Asp Glu Val Phe Lys Ile Glu
                 270                 275                 280 cgg ccg ggt gaa ggg agc ccc atg gtt gac aac ccc atg aga cgg aag            975
Arg Pro Gly Glu Gly Ser Pro Met Val Asp Asn Pro Met Arg Arg Lys
             285                 290                 295 agc ggg ccg tcc tgc aag cac tgc aag gac gac gtg aac aga ctc tgc           1023
Ser Gly Pro Ser Cys Lys His Cys Lys Asp Asp Val Asn Arg Leu Cys
         300                 305                 310 cgg gtc tgc gcc tgc cac ctg tgc ggg gcc cgg cag gac ccc gac aag           1071
Arg Val Cys Ala Cys His Leu Cys Gly Gly Arg Gln Asp Pro Asp Lys
     315                 320                 325 cag ctc atg tgc gat gag tgc gac atg gcc ttc cac atc tac tgc ctg           1119
Gln Leu Met Cys Asp Glu Cys Asp Met Ala Phe His Ile Tyr Cys Leu
330                 335                 340                 345
```

```
gac ccg ccc ctc agc agt gtt ccc agc gag gac gag tgg tac tgc cct        1167
Asp Pro Pro Leu Ser Ser Val Pro Ser Glu Asp Glu Trp Tyr Cys Pro
            350                 355                 360 gag tgc cgg aat gat gcc agc gag gtg gta ctg gcg gga gag cgg ctg        1215
Glu Cys Arg Asn Asp Ala Ser Glu Val Val Leu Ala Gly Glu Arg Leu
        365                 370                 375 aga gag agc aag aag aag gcg aag atg gcc tcg gcc aca tcg tcc tca        1263
Arg Glu Ser Lys Lys Lys Ala Lys Met Ala Ser Ala Thr Ser Ser Ser
    380                 385                 390 cag cgg gac tgg ggc aag ggc atg gcc tgt gtg ggc cgc acc aag gaa        1311
Gln Arg Asp Trp Gly Lys Gly Met Ala Cys Val Gly Arg Thr Lys Glu
395                 400                 405 tgt acc atc gtc ccg tcc aac cac tac gga ccc atc ccg ggg atc ccc        1359
Cys Thr Ile Val Pro Ser Asn His Tyr Gly Pro Ile Pro Gly Ile Pro
410                 415                 420                 425 gtg ggc acc atg tgg cgg ttc cga gtc cag gtc agc gag tcg ggt gtc        1407
Val Gly Thr Met Trp Arg Phe Arg Val Gln Val Ser Glu Ser Gly Val
            430                 435                 440 cat cgg ccc cac gtg gct ggc ata cac ggc cgg agc aac gac gga gcg        1455
His Arg Pro His Val Ala Gly Ile His Gly Arg Ser Asn Asp Gly Ala
        445                 450                 455 tac tcc cta gtc ctg gcg ggg ggc tat gag gat gac gtg gac cat ggg        1503
Tyr Ser Leu Val Leu Ala Gly Gly Tyr Glu Asp Asp Val Asp His Gly
    460                 465                 470 aat ttt ttc aca tac acg ggt agt ggt ggt cga gat ctt tcc ggc aac        1551
Asn Phe Phe Thr Tyr Thr Gly Ser Gly Gly Arg Asp Leu Ser Gly Asn
475                 480                 485 aag agg acc gcg gaa cag tct tgt gat cag aaa ctc acc aac acc aac        1599
Lys Arg Thr Ala Glu Gln Ser Cys Asp Gln Lys Leu Thr Asn Thr Asn
490                 495                 500                 505 agg gcg ctg gct ctc aac tgc ttt gct ccc atc aat gac caa gaa ggg        1647
Arg Ala Leu Ala Leu Asn Cys Phe Ala Pro Ile Asn Asp Gln Glu Gly
            510                 515                 520 gcc gag gcc aag gac tgg cgg tcg ggg aag ccg gtc agg gtg gtg cgc        1695
Ala Glu Ala Lys Asp Trp Arg Ser Gly Lys Pro Val Arg Val Val Arg
        525                 530                 535 aat gtc aag ggt ggc aag aat agc aag tac gcc ccc gct gag ggc aac        1743
Asn Val Lys Gly Gly Lys Asn Ser Lys Tyr Ala Pro Ala Glu Gly Asn
    540                 545                 550 cgc tac gat ggc atc tac aag gtt gtg aaa tac tgg ccc gag aag ggg        1791
Arg Tyr Asp Gly Ile Tyr Lys Val Val Lys Tyr Trp Pro Glu Lys Gly
555                 560                 565 aag tcc ggg ttt ctc gtg tgg cgc tac ctt ctg cgg agg gac gat gat        1839
Lys Ser Gly Phe Leu Val Trp Arg Tyr Leu Leu Arg Arg Asp Asp Asp
570                 575                 580                 585 gag cct ggc cct tgg acg aag gag ggg aag gac cgg atc aag aag ctg        1887
Glu Pro Gly Pro Trp Thr Lys Glu Gly Lys Asp Arg Ile Lys Lys Leu
            590                 595                 600 ggg ctg acc atg cag tat cca gaa ggc tac ctg gaa gcc ctg gcc aac        1935
Gly Leu Thr Met Gln Tyr Pro Glu Gly Tyr Leu Glu Ala Leu Ala Asn
        605                 610                 615 cga gag cga gag aag gag aac agc aag agg gag gag gag cag cag        1983
Arg Glu Arg Glu Lys Glu Asn Ser Lys Arg Glu Glu Glu Gln Gln
    620                 625                 630 gag ggg ggc ttc gcg tcc ccc agg acg ggc aag ggc aag tgg aag cgg        2031
Glu Gly Gly Phe Ala Ser Pro Arg Thr Gly Lys Gly Lys Trp Lys Arg
635                 640                 645 aag tcg gca gga ggt ggc ccg agc agg gcc ggg tcc ccg cgc cgg aca        2079
Lys Ser Ala Gly Gly Gly Pro Ser Arg Ala Gly Ser Pro Arg Arg Thr
650                 655                 660                 665
```

| | |
|---|---|
| tcc aag aaa acc aag gtg gag ccc tac agt ctc acg gcc cag cag agc<br>Ser Lys Lys Thr Lys Val Glu Pro Tyr Ser Leu Thr Ala Gln Gln Ser<br>             670               675                680 | 2127 |
| agc ctc atc aga gag gac aag agc aac gcc aag ctg tgg aat gag gtc<br>Ser Leu Ile Arg Glu Asp Lys Ser Asn Ala Lys Leu Trp Asn Glu Val<br>         685                 690               695 | 2175 |
| ctg gcg tca ctc aag gac cgg ccg gcg agc ggc agc ccg ttc cag ttg<br>Leu Ala Ser Leu Lys Asp Arg Pro Ala Ser Gly Ser Pro Phe Gln Leu<br>700                     705               710 | 2223 |
| ttc ctg agt aaa gtg gag gag acg ttc cag tgt atc tgc tgt cag gag<br>Phe Leu Ser Lys Val Glu Glu Thr Phe Gln Cys Ile Cys Cys Gln Glu<br>             715               720             725 | 2271 |
| ctg gtg ttc cgg ccc atc acg acc gtg tgc cag cac aac gtg tgc aag<br>Leu Val Phe Arg Pro Ile Thr Thr Val Cys Gln His Asn Val Cys Lys<br>730                     735               740             745 | 2319 |
| gac tgc ctg gac aga tcc ttt cgg gca cag gtg ttc agc tgc cct gcc<br>Asp Cys Leu Asp Arg Ser Phe Arg Ala Gln Val Phe Ser Cys Pro Ala<br>         750                 755               760 | 2367 |
| tgc cgc tac gac ctg ggc cgc agc tat gcc atg cag gtg aac cag cct<br>Cys Arg Tyr Asp Leu Gly Arg Ser Tyr Ala Met Gln Val Asn Gln Pro<br>             765               770             775 | 2415 |
| ctg cag acc gtc ctc aac cag ctc ttc ccc ggc tac ggc aat ggc cgg<br>Leu Gln Thr Val Leu Asn Gln Leu Phe Pro Gly Tyr Gly Asn Gly Arg<br>780                     785               790 | 2463 |
| tga ctccaagca cttctcgaca ggcgttttgc tgaaaacgtg tcggagggct | 2516 |
| cgttcatcgg cactgatttt gttcttagtg ggcttaactt aaacaggtag tgtttcctcc | 2576 |
| gttccctaaa aaggtttgtc ttcctttttt tttatttttta ttttcaaat ctatacattt | 2636 |
| tcaggaattt atgtattctg gctaaaagtt ggacttctca gtattgtgtt tagttctttg | 2696 |
| aaaacataaa agcctgcaat ttctcgacaa acaacacaa gatttttaa agatggaatc | 2756 |
| agaaactacg tggtgtggag gctgttgatg tttctggtgt caagttctca gaagttgctg | 2816 |
| ccaccaactc tttaagaagg cgacaggatc agtccttctc tagggttctg gcccccaagg | 2876 |
| tcagagcaag catcttcctg acagcatttt gtcatctaaa gtccagtgac atggttcccc | 2936 |
| gtggtggccc gtggcagccc gtggcatggc gtggctcagc tgtctgttga gttgttgca | 2996 |
| aggaaaagag gaaacatctc gggcctagtt caaacctttg cctcaaagcc atccccacc | 3056 |
| agactgctta gcgtctgaga tccgcgtgaa aagtcctctg cccacgagag cagggagttg | 3116 |
| gggccacgca gaaatggcct caaggggact ctgctccacg tggggccagg cgtgtgactg | 3176 |
| acgctgtccg acgaaggcgg ccacggacgg acgccagcac acgaagtcac gtgcaagtgc | 3236 |
| ctttgattcg ttccttcttt ctaaagacga cagtctttgt tgttagcact gaattattga | 3296 |
| aaatgtcaac cagattctag aaactgcggt catccagttc ttcctgacac cggatgggtg | 3356 |
| cttgggaacc gtttgagcct tatagatcat ttacattcaa ttttttttaac tcagcaagtg | 3416 |
| agaacttaca agagggtttt ttttttaattt ttttttctct taatgaacac attttctaaa | 3476 |
| tgaatttttt ttgtagttac tgtatatgta ccaagaaaga tataacgtta gggtttggtt | 3536 |
| gttttttgttt ttgtattttt tttcttttga aagggtttgt taattttttct aattttacca | 3596 |
| aagtttgcag cctatacctc aataaaacag ggatattta aatcacatac ctgcagacaa | 3656 |
| actggagcaa tgttattttt aaagggtttt tttcacctcc ttattcttag attattaatg | 3716 |
| tattagggaa gaatgagaca attttgtgta ggcttttttct aaagtccagt actttgtcca | 3776 |
| gattttagat tctcagaata aatgttttc acagattgaa aaaaaaaaa aa | 3828 |

<210> SEQ ID NO 2
<211> LENGTH: 793
<212> TYPE: PRT
<213> ORGANISM: Homo sapiens
<220> FEATURE:
<223> OTHER INFORMATION: human NP95 nuclear zinc finger protein

<400> SEQUENCE: 2

```
Met Trp Ile Gln Val Arg Thr Met Asp Gly Arg Gln Thr His Thr Val
 1               5                  10                  15

Asp Ser Leu Ser Arg Leu Thr Lys Val Glu Glu Leu Arg Arg Lys Ile
                20                  25                  30

Gln Glu Leu Phe His Val Glu Pro Gly Leu Gln Arg Leu Phe Tyr Arg
            35                  40                  45

Gly Lys Gln Met Glu Asp Gly His Thr Leu Phe Asp Tyr Glu Val Arg
    50                  55                  60

Leu Asn Asp Thr Ile Gln Leu Val Arg Gln Ser Leu Val Leu Pro
65                  70                  75                  80

His Ser Thr Lys Glu Arg Asp Ser Glu Leu Ser Asp Thr Asp Ser Gly
                85                  90                  95

Cys Cys Leu Gly Gln Ser Glu Ser Asp Lys Ser Ser Thr His Gly Glu
            100                 105                 110

Ala Ala Ala Glu Thr Asp Ser Arg Pro Ala Asp Glu Asp Met Trp Asp
        115                 120                 125

Glu Thr Glu Leu Gly Leu Tyr Lys Val Asn Glu Tyr Val Asp Ala Arg
    130                 135                 140

Asp Thr Asn Met Gly Ala Trp Phe Glu Ala Gln Val Val Arg Val Thr
145                 150                 155                 160

Arg Lys Ala Pro Ser Arg Asp Glu Pro Cys Ser Ser Thr Ser Arg Pro
                165                 170                 175

Ala Leu Glu Glu Asp Val Ile Tyr His Val Lys Tyr Asp Asp Tyr Pro
            180                 185                 190

Glu Asn Gly Val Val Gln Met Asn Ser Arg Asp Val Arg Ala Arg Ala
        195                 200                 205

Arg Thr Ile Ile Lys Trp Gln Asp Leu Glu Val Gly Gln Val Val Met
    210                 215                 220

Leu Asn Tyr Asn Pro Asp Asn Pro Lys Glu Arg Gly Phe Trp Tyr Asp
225                 230                 235                 240

Ala Glu Ile Ser Arg Lys Arg Glu Thr Arg Thr Ala Arg Glu Leu Tyr
                245                 250                 255

Ala Asn Val Val Leu Gly Asp Asp Ser Leu Asn Asp Cys Arg Ile Ile
            260                 265                 270

Phe Val Asp Glu Val Phe Lys Ile Glu Arg Pro Gly Glu Gly Ser Pro
        275                 280                 285

Met Val Asp Asn Pro Met Arg Arg Lys Ser Gly Pro Ser Cys Lys His
    290                 295                 300

Cys Lys Asp Asp Val Asn Arg Leu Cys Arg Val Cys Ala Cys His Leu
305                 310                 315                 320

Cys Gly Gly Arg Gln Asp Pro Asp Lys Gln Leu Met Cys Asp Glu Cys
                325                 330                 335

Asp Met Ala Phe His Ile Tyr Cys Leu Asp Pro Pro Leu Ser Ser Val
            340                 345                 350

Pro Ser Glu Asp Glu Trp Tyr Cys Pro Glu Cys Arg Asn Asp Ala Ser
        355                 360                 365
```

```
Glu Val Val Leu Ala Gly Glu Arg Leu Arg Glu Ser Lys Lys Ala
    370             375             380
Lys Met Ala Ser Ala Thr Ser Ser Ser Gln Arg Asp Trp Gly Lys Gly
385             390             395             400
Met Ala Cys Val Gly Arg Thr Lys Glu Cys Thr Ile Val Pro Ser Asn
            405             410             415
His Tyr Gly Pro Ile Pro Gly Ile Pro Val Gly Thr Met Trp Arg Phe
            420             425             430
Arg Val Gln Val Ser Glu Ser Gly Val His Arg Pro His Val Ala Gly
        435             440             445
Ile His Gly Arg Ser Asn Asp Gly Ala Tyr Ser Leu Val Leu Ala Gly
    450             455             460
Gly Tyr Glu Asp Asp Val Asp His Gly Asn Phe Phe Thr Tyr Thr Gly
465             470             475             480
Ser Gly Gly Arg Asp Leu Ser Gly Asn Lys Arg Thr Ala Glu Gln Ser
            485             490             495
Cys Asp Gln Lys Leu Thr Asn Thr Asn Arg Ala Leu Ala Leu Asn Cys
            500             505             510
Phe Ala Pro Ile Asn Asp Gln Glu Gly Ala Glu Ala Lys Asp Trp Arg
            515             520             525
Ser Gly Lys Pro Val Arg Val Val Arg Asn Val Lys Gly Gly Lys Asn
530             535             540
Ser Lys Tyr Ala Pro Ala Glu Gly Asn Arg Tyr Asp Gly Ile Tyr Lys
545             550             555             560
Val Val Lys Tyr Trp Pro Glu Lys Gly Lys Ser Gly Phe Leu Val Trp
            565             570             575
Arg Tyr Leu Leu Arg Arg Asp Asp Asp Glu Pro Gly Pro Trp Thr Lys
        580             585             590
Glu Gly Lys Asp Arg Ile Lys Lys Leu Gly Leu Thr Met Gln Tyr Pro
    595             600             605
Glu Gly Tyr Leu Glu Ala Leu Ala Asn Arg Glu Arg Glu Lys Glu Asn
    610             615             620
Ser Lys Arg Glu Glu Glu Glu Gln Gln Glu Gly Gly Phe Ala Ser Pro
625             630             635             640
Arg Thr Gly Lys Gly Lys Trp Lys Arg Lys Ser Ala Gly Gly Gly Pro
            645             650             655
Ser Arg Ala Gly Ser Pro Arg Arg Thr Ser Lys Lys Thr Lys Val Glu
            660             665             670
Pro Tyr Ser Leu Thr Ala Gln Gln Ser Ser Leu Ile Arg Glu Asp Lys
            675             680             685
Ser Asn Ala Lys Leu Trp Asn Glu Val Leu Ala Ser Leu Lys Asp Arg
690             695             700
Pro Ala Ser Gly Ser Pro Phe Gln Leu Phe Leu Ser Lys Val Glu Glu
705             710             715             720
Thr Phe Gln Cys Ile Cys Cys Gln Glu Leu Val Phe Arg Pro Ile Thr
            725             730             735
Thr Val Cys Gln His Asn Val Cys Lys Asp Cys Leu Asp Arg Ser Phe
            740             745             750
Arg Ala Gln Val Phe Ser Cys Pro Ala Cys Arg Tyr Asp Leu Gly Arg
        755             760             765
Ser Tyr Ala Met Gln Val Asn Gln Pro Leu Gln Thr Val Leu Asn Gln
    770             775             780
Leu Phe Pro Gly Tyr Gly Asn Gly Arg
```

-continued

```
785                 790
```

<210> SEQ ID NO 3
<211> LENGTH: 136
<212> TYPE: PRT
<213> ORGANISM: Artificial Sequence
<220> FEATURE:
<223> OTHER INFORMATION: Description of Artificial Sequence:G1-2635

<400> SEQUENCE: 3

```
Ala Glu Gln Ser Cys Asp Gln Lys Leu Thr Asn Thr Asn Arg Ala Leu
 1               5                  10                  15

Ala Leu Asn Cys Phe Ala Pro Ile Asn Asp Gln Glu Gly Ala Glu Ala
            20                  25                  30

Lys Asp Trp Arg Ser Gly Lys Pro Val Arg Val Arg Asn Val Lys
        35                  40                  45

Gly Gly Lys Asn Ser Lys Tyr Ala Pro Ala Glu Gly Asn Arg Tyr Asp
    50                  55                  60

Gly Ile Tyr Lys Val Val Lys Tyr Trp Pro Glu Lys Gly Lys Ser Gly
 65                 70                  75                  80

Phe Leu Val Trp Arg Tyr Leu Leu Arg Arg Asp Asp Asp Glu Pro Gly
                85                  90                  95

Pro Trp Thr Lys Glu Gly Lys Asp Arg Ile Lys Lys Leu Gly Leu Thr
            100                 105                 110

Met Gln Tyr Pro Glu Gly Tyr Leu Glu Ala Leu Ala Asn Arg Glu Arg
        115                 120                 125

Glu Lys Glu Asn Ser Lys Arg Glu
    130                 135
```

<210> SEQ ID NO 4
<211> LENGTH: 200
<212> TYPE: PRT
<213> ORGANISM: Artificial Sequence
<220> FEATURE:
<223> OTHER INFORMATION: Description of Artificial Sequence:poly Gly
      flexible linker
<220> FEATURE:
<221> NAME/KEY: MOD_RES
<222> LOCATION: (6)..(200)
<223> OTHER INFORMATION: Gly residues from position 6 to 200 may be
      present or absent

<400> SEQUENCE: 4

```
Gly Gly Gly Gly Gly Gly Gly Gly Gly Gly Gly Gly Gly Gly Gly Gly
 1               5                  10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly Gly
 65                 70                  75                  80

Gly Gly Gly Gly Gly Gly Gly Gly Gly Gly Gly Gly Gly Gly Gly Gly
                85                  90                  95

Gly Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125
```

```
                                                -continued

Gly Gly Gly Gly Gly Gly Gly Gly Gly Gly Gly Gly Gly Gly Gly
        130                 135                 140

Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly
            165                 170                 175

Gly Gly Gly Gly Gly Gly Gly Gly Gly Gly Gly Gly Gly Gly Gly
                180                 185                 190

Gly Gly Gly Gly Gly Gly Gly Gly
        195                 200
```